(12) United States Patent
Kurek et al.

(10) Patent No.: US 6,670,509 B1
(45) Date of Patent: Dec. 30, 2003

(54) CONVERSION OF ORGANIC SUBSTRATES TO OXYGENATES OR OLEFINS USING A BICYCLO IMIDE PROMOTER

(75) Inventors: Paul R. Kurek, Barrington, IL (US); David W. House, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 60 days.

(21) Appl. No.: 10/120,821

(22) Filed: Apr. 11, 2002

(51) Int. Cl.⁷ .............................................. C07C 45/00
(52) U.S. Cl. ........................ 568/320; 568/322; 568/347; 568/357; 568/385; 568/398.8; 568/399; 568/403; 568/430; 568/431; 568/469.9; 568/470; 568/485; 568/814; 568/884
(58) Field of Search ................................ 568/320, 357, 568/322, 347, 385, 398.8, 399, 403, 430, 431, 469.9, 470, 485, 814, 884

(56) References Cited

U.S. PATENT DOCUMENTS 5,958,821 A 9/1999 Ishii et al. .................. 502/167
6,037,507 A 3/2000 Nakano et al. .......... 568/910.5

OTHER PUBLICATIONS

Murahashi et al., *J. Chem. Soc. Chem. Commun.*, 1993, 139–140.
*Catalysis Letters* 8 1991,45–52.
Murahashi et al., *Tetrahedron Letters* 1993, 34(8) 1299–1302.
Khirnova et al., *Petrol. Chem. U.S.R.R.* 1981, 21(1), 49–52.
Ishii et al. *Catalysis Surveys from Japan 3* 1999, 27–35.
Ishii et al., *J. Org. Chem.* 1996, 61, 4520–4526.
*J. Phys. Chem. A* 2001, 105, 5881–5884.

Primary Examiner—Samuel Barts
(74) Attorney, Agent, or Firm—John G. Tolomei; Frank S. Molinaro

(57) ABSTRACT

A process for oxygenating organic substrates such as aliphatic hydrocarbons has been developed. The process involves contacting the organic substrate with oxygen in the presence of a bicyclo imide promoter and a metal co-catalyst. The process is preferably carried out using sulfolane as the solvent. Optionally, the oxygenated product can be hydrogenated to give the corresponding alcohol which can optionally in turn be dehydrated to provide the corresponding olefin.

32 Claims, 1 Drawing Sheet

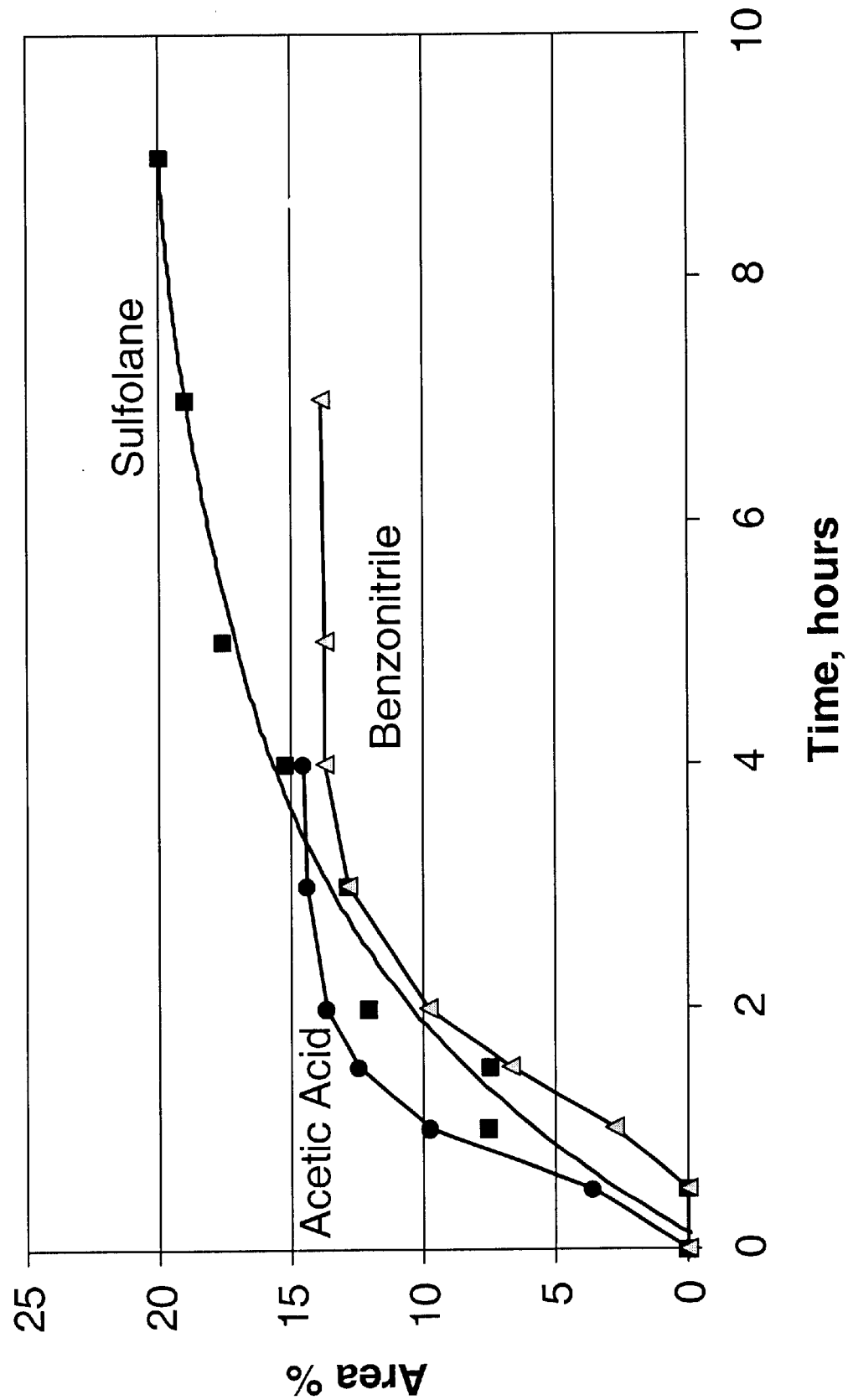

CONVERSION OF ORGANIC SUBSTRATES TO OXYGENATES OR OLEFINS USING A BICYCLO IMIDE PROMOTER

FIELD OF THE INVENTION

This invention relates to a process for reacting various organic substrates with oxygen in the presence of a catalyst comprising a bicyclo imide promoter and a metal co-catalyst to provide an oxygenated product. The oxygenated product, e.g. ketone or aldehyde can be further reacted with hydrogen to form the corresponding alcohol and the alcohol can be dehydrated to provide the corresponding olefin.

BACKGROUND OF THE INVENTION

Organic compounds containing an oxygen in the structure have various industrial uses either in and of themselves or as precursors to more valuable products. These oxygenated organic compounds are usually prepared by processes which convert hydrocarbons to the oxygen containing organic compounds. Although saturated hydrocarbons such as paraffins and branched paraffins are the lowest cost and most readily available hydrocarbons, they are also very stable and thus not very chemically reactive. In particular, linear paraffinic compounds are the hardest to oxygenate. It would be very desirable to easily convert paraffins (and especially linear paraffins) to oxygenates.

There are a number of reports in the literature of various ways to oxidize hydrocarbons to the corresponding aldehyde or ketone. One reference is U.S. Pat. No. 5,958,821 which discloses oxidizing various hydrocarbons such as cycloalkanes, aromatic hydrocarbons, etc. with oxygen in the presence of an oxidation catalyst comprising an imide compound such N-hydroxyphthalimide and a metal compound co-catalyst such as cobalt or manganese acetyl acetonate. The patentee of the '821 reference enumerates virtually every class of known hydrocarbons and virtually every metal in the periodic table. Other references which have addressed the oxygenation of alkanes include Shun-Ichi Murahashi et al. in *J. Chem. Soc, Chem. Commun.*,(1993) 139–140 in which the authors present results for the oxidation of alkanes and alkenes with oxygen in the presence of aldehydes and using a copper compound catalyst. Their results showed that linear alkanes such as n-decane had extremely low conversion. In *Catalysis Letters* 8 (1991), 45–52 the same authors have shown that isobutane can react with oxygen in the presence of an iron perhaloporphyrin complex to give mostly tert-butyl alcohol. Shun-Ichi Murahashi et al. have reported in *Tetrahedron Letters,* (1993), vol. 34, no. 8 pp. 1299–1302, 1993 the ruthenium catalyzed oxidation of alkanes with alkyl hydroperoxide. Specifically, they reacted n-heptane and n-decane to provide ketones and alcohols. G. P. Khimova et al. in *Petrol. Chem U.S.R.R.* (1981), vol. 21, no. 1, pp. 49–52 have reported the liquid phase oxidation of isobutane using a heterogeneous catalyst containing cobalt and molybdenum borides or molybdenum carbides. The main products of this reaction were tert-butyl hydroperoxides, tert-butyl alcohol and acetone. It has also been shown in U.S. Pat. No. 5,395,980 that isobutane can be converted to tert-butyl hydroperoxide at elevated temperatures (about 140° C.) by reacting it with oxygen in the presence of tert-butyl alcohol and di (tert-butyl) peroxide.

There are also reports of the oxidation of alkanes with oxygen using N-hydroxyphthalimide (NHPI) as a catalyst and a metal compound co-catalyst. For example, Y. Ishii et al. in *Catalysis Surveys from Japan* 3 (1999) 27–35 report the oxidation of various alkanes including isobutane. The isobutane gave tert-butyl alcohol and acetone and tert-butyl hydroperoxide. The other alkanes which were tested were all branched alkanes. Ishii et al. in *J. Org. Chem.*(1996), 61, 4520–4526 present results of the oxidation of various cycloalkanes using NHPI and Co(acac)$_n$. Results are also presented for the oxidation of n-octane to give octanols and octanones. Further, U.S. Pat. No. 6,037,507 discloses the oxidation of branched aliphatic hydrocarbons using an imide promoter. It has also been reported that aromatic compounds such as p-xylene can be oxidized to carboxylic acids by using a mixed metal catalyst. See e.g. *J. Phys. ChemA* 2001, 105 5881–5884.

Applicants have found that the use of a bicyclo imide compound having two NHPI units gives improved results versus using twice the equivalent of NHPI itself. Applicants have further found that the use of solvents such as sulfolane provides improved activity versus acetic acid.

SUMMARY OF THE INVENTION

As stated, the present invention relates to a process for converting organic substrates to oxygenated compounds and then optionally converting the oxygenated compounds to olefins. Accordingly, one embodiment of the invention is a process for converting an organic substrate to an oxygenated compound comprising reacting the organic substrate with an oxygen source in the presence of a catalyst comprising an imide promoter and a co-catalyst at oxidation conditions to provide an oxygenated compound, the imide promoter being represented by at least one of structures (I), (II), (III), or (IV):

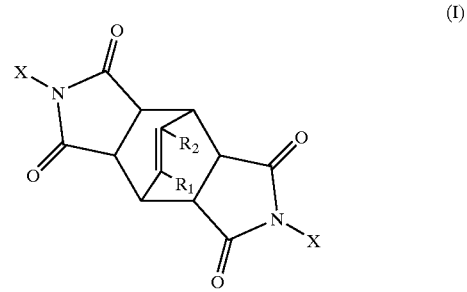

(I)

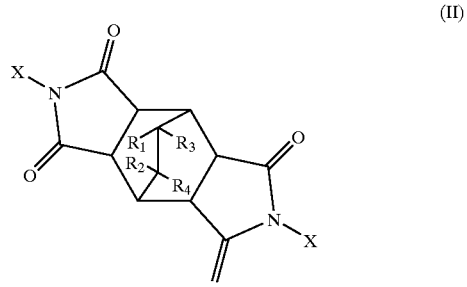

(II)

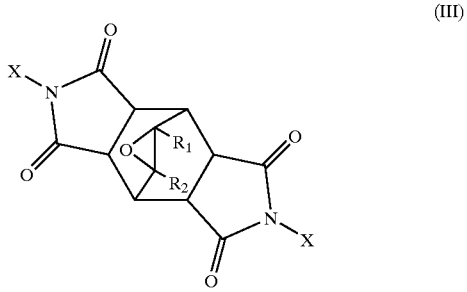

(III)

-continued

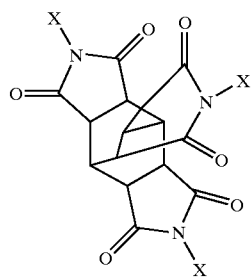
(IV)

where $R_1$, $R_2$, $R_3$ and $R_4$ are independently selected from the group consisting of hydrogen, halogens, alkyl groups, cycloalkyl groups, aryl groups, sulfonyl groups, sulfonic acid, hydroxyl groups, alkoxy groups, carboxyl groups, ethers, amines, amides, alkoxy-carbonyl groups and acyl groups; and X is selected from the group consisting of O, OH, acetyl, acetoxy, ether and halogen and the co-catalyst comprising at least one metal selected from the group consisting of Groups IB, IVB, VB, VIB, VIIB and VIII metals of the Periodic Table of the Elements.

Another embodiment of the invention is to take the oxygenated compound of the previous paragraph and react it with hydrogen in the presence of a hydrogenation catalyst at hydrogenation conditions to provide alcohols and then optionally contacting the alcohols with a dehydrogenation catalyst to provide olefins.

These and other objects and embodiments will become clearer after a detailed description of the invention.

DETAILED DESCRIPTION OF THE INVENTION

One essential part of the present invention is a catalyst which comprises an imide promoter and a co-catalyst. The imide promoter has at least one of the structures below.

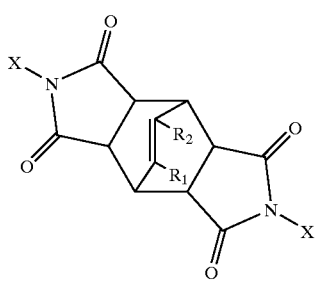
(I)

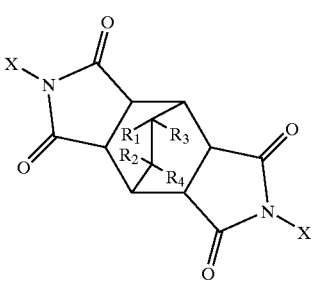
(II)

-continued

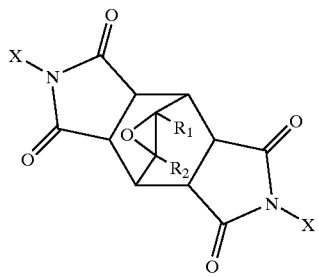
(III)

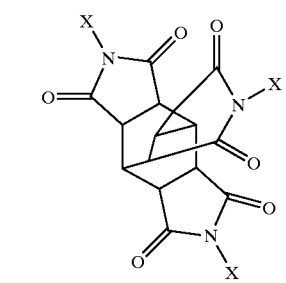
(IV)

where $R_1$, $R_2$, $R_3$ and $R_4$ are independently selected from the group consisting of hydrogen, halogens, alkyl groups, cycloalkyl groups, aryl groups, sulfonyl group, sulfonic acid, hydroxyl groups, alkoxy groups, carboxyl groups, ethers, amines, amides, alkoxy-carbonyl groups and acyl groups; and the co-catalyst comprising at least one metal selected from the groups consisting of Groups IB, IVB, VB, VIB, VIIB and VIII metals of the Periodic Table of the Elements. X is selected from the group consisting of O, OH, acetyl, acetoxy, ether and halogen.

In any of the imide structures I to IV, when $R_1$, $R_2$, $R_3$ and/or $R_4$ represent halogens, these include iodine, bromine, chlorine and fluorine. Alkyl groups include without limitations, methyl, ethyl, propyl, isopropyl, butyl, isobutyl, hexyl, heptyl, other straight chains or branched chain alkyl groups having alkyl branches of 1 to 10 carbon atoms, preferably 1 to 6 carbon atoms and most preferably 1 to 4 carbon atoms.

Specific examples of aryl or aromatic groups, without limitation, are phenyl groups and naphthyl groups. Cycloalkyl groups include without limitation cyclopentyl, cyclohexyl, cyclooctyl, etc. Specific examples of alkoxy groups include methoxy, ethoxy, propoxy, butoxy, isobutoxy, isopropoxy and other alkoxy groups having from 1 to 10 carbon atoms, preferably 1 to 6 carbon atoms and most preferably 1 to 4 carbon atoms. Alkoxy-carbonyl groups include those having 1 to 10 carbon atoms, preferably 1 to 6 carbon atoms and most preferably 1 to 4 carbon atoms. Specific examples include, without limitation, methoxy carbonyl, ethoxy carbonyl, isopropoxy carbonyl, pentyl oxycarbonxyl, etc. Acyl groups are any of those containing 1 to 6 carbon atoms and include formyl, acetyl, propionyl, isobutyryl, etc.

These imide compounds can be prepared by conventional methods in which an acid anhydride reacts with a hydroxylamine to give an imide. Some of these imides are commercially available. A preferred bicyclo imide is N,N'-dihydroxy-bicyclo[2.2.2]oct-7-ene-2,3,5,6-tetracarboxylic diimide.

Another essential element of the catalyst of this invention is a co-catalyst comprising a metal. The metals which can be used as the co-catalyst are any of the metals from groups IB, IVB, VB, VIB, VIIB and VIII of the Periodic Table of the Elements (IUPAC 4 to 10) and preferably group VII (IUPAC 8 to 10). The two nomenclatures for the Periodic Table are those set forth in the Periodic Table published by the Los Alamos National Laboratory and available on the Internet at the URL http://pearl 1.lanl.gov/periodic/. Preferred metals include without limitation Co, Mn, Ti, V, Zr, Cr, Mo, W, Re, Ru, Rh, Mg, Cu and mixtures thereof. These metals can be used homogeneously or heterogeneously. When used homogeneously, the metals are present as salts or chelated compounds. Non-limiting examples of salts are acetates, nitrates, sulfates, carbonates and halides. Non-limiting examples of chelates which can form complexes with the metals are acetylacetonate, porphyrins, phthalocyanines, crown ethers, ferrocene and mixtures thereof.

Heterogeneous systems involve depositing the desired metal onto a support which has a sufficient surface area to disperse the metal but which is not affected by the solvents, reactants or products, i.e. refractory supports. The surface area (as measured by the B.E.T. method) should be greater than $5m^2/g$ and preferably from about 10 $m^2/g$ to about 500 $m^2/g$. Non-limiting examples of these refractory supports are aluminas, silica, carbon, zirconia, zeolites and clays. The desired metal is dispersed on the support by conventional methods such as impregnation, co-precipitation, spray drying, etc. A common method is to impregnate the support with a solution containing a metal salt or chelate, drying and calcining the impregnated support. The metal can be present on the support as the metal, i.e. zero valent state, the oxide or a compound.

The amount of imide and co-catalyst can vary widely with the imide usually varying from about 0.05 to about 20 mole % with respect to the organic substrate and the co-catalyst usually varying from about 0.005 to about 0.015 mole % as the metal with respect to the organic substrate.

The organic substrates which can be used in the instant process can vary widely but generally include without limitation aliphatic, alicyclic and aromatic hydrocarbons, heterocyclic compounds, alcohols, ethers, esters, ketones, aldehydes, amines and mixtures thereof. These substrates can in turn be substituted with one or more of the following without limitation: halogens, alkyl groups, oxo groups, hydroxyl groups, alkoxy groups, hydroxy-acyl groups, cyano groups, nitro groups, sulfate groups, phosphate groups, etc. The aliphatic hydrocarbons include both linear and branched compounds as well as saturated and unsaturated compounds. Although the number of carbon atoms can vary considerably, commercially useful aliphatic compounds have from 1 to 30 carbon atoms and preferably 2 to 20 carbon atoms. When the aliphatic compound is branched, the branch can have from one to 6 and preferably one to four (4) carbon atoms. Of course the aliphatic compound can have more than one branch. Specific examples of the linear aliphatic compounds include without limitation, methane, ethane, propane, butenes, butane, pentenes, pentanes, hexenes, hexanes, heptenes, heptanes, octenes, octanes, nonenes, nonanes, decenes, decanes, dodecane, etc.

Alicyclic compounds which can be used include any of those having from 3 to 30 carbons, preferably 5 to 25 carbons and most preferably 6 to 20 carbons. Specific examples of unsubstituted and substituted compounds include without limitation cyclopropane, cyclobutane, cyclopentane, cyclohexane, cycloheptane, cyclooctane, cyclohexanol, cyclooctanol, cyclopentanone, cyclohexanone, cyclooctanone, adamantane, decalin, etc.

Aromatic compounds which can be used in the instant process are any of those that have at least one alkyl group attached to the aromatic ring. The aromatic ring includes heterocyclic rings. Usually the alkyl group attached to the aromatic ring is a methyl group, but groups with up to ten and preferably up to six carbon atoms can also be used. These alkyl groups can be linear, branched and cyclic alkyl groups. Specific examples include without limitation toluene, xylenes, 1,2,3-trimethylbenzene, ethylbenzene, diethylbenzene, o-,m-, or p-methylethylbenzene, 1-methylnaphthalene, 1,5 dimethylnaphthalene, 1-methyl 5-ethyl naphthalene, methylanthracene, dimethylanthracene, tetralin, other aromatic rings containing fused aliphatic rings, etc. Heterocyclic compounds which can be used are those which also have at least one alkyl group attached to the ring. Specific examples without limitation include 2-methylfuran, 3-methylfuran, 2-ethylfuran, 2-methylpyran, 2-methylpyridine, 3-methylpyridine, 2-ethylpyridine, 2,3-dimethylpyridine, 2-methyl-3-ethylpyridine, etc.

As was stated above, any of these organic substrates may have further substituents attached to them. Specific examples again without limitation include for halogens: iodine, bromine, chlorine and fluorine; for alkoxy groups: methoxy, ethoxy, propoxy, isopropoxy, etc.; for hydroxyalkyl groups: hydroxymethyl, 2-hydroxyethyl, etc.; for alkylcarbonyl groups: methoxycarbonyl, ethoxycarbonyl, propoxycarbonyl, isopropoxycarbonyl, etc.; for acyl groups: formyl, acetyl, propionyl, butyryl, isobutyryl, etc.

As stated the desired organic substrate is reacted with an oxygen source in order to form oxygenated products. The oxygen source can be pure oxygen or any source of oxygen such as air, hydrogen peroxide, ozone, organic peroxides, nitric oxide, etc. The amount of oxygen which is needed to carry out the oxidation ranges from about 0.5 to about 100 moles per mole of substrate (0.5:1 to 100:1) and preferably from about 2 to about 50 moles per mole of substrate (2:1 to 50:1). It is desirable to have an excess amount of oxygen.

The oxidation process of the invention can be conducted without solvent, i.e. the organic substrate acts as the solvent, but is preferably conducted in an organic solvent. Examples of these solvents include without limitation, acetic acid, propionic acid, other carboxylic acids, hydroxycarboxylic acids, nitriles such as acetonitrile, benzonitrile, amides such as acetamide, dimethylformamide (DMF), alkyl acetates, etc. Applicants have found that an especially preferred family of solvents are sulfones. Examples of sulfones which can be used without limitation, include: sulfolane; substituted sulfolanes such as 2,4-dimethylsulfolane; dimethyl sulfone; butadiene sulfone, etc. Sulfolane is an especially preferred solvent. The preferred sulfone solvents have been found to be useful regardless of what type of imide promoter is used i.e. bicyclo or non-bicyclo. Although it is preferred to carry out the instant process using a solvent, the process can be carried out using the substrates as the solvent.

The oxidation conditions for carrying out the process of the invention can vary considerably. The temperature for example can vary from about 30° C. to about 300° C., preferably from about 50° C. to about 200° C. and most preferably from about 70° C. to about 150° C. Although the reaction can be carried out at atmospheric pressure it can also be carried out at elevated pressures in the range of about 10 kPa to about 100 MPa, preferably from about 500 kPa to about 50 MPa. The process can be carried out in a batch mode, a semi-batch mode or continuous flow mode in the presence of an oxygen source or under a steady flow of an oxygen source. In a batch mode, the desired reactants are contacted for a sufficient time to obtain adequate conversion of the organic substrate, which is usually from about 30 minutes to about 48 hours, preferably from about 1 to 36 hours and more preferably from about 2 to about 24 hours. In a continuous mode a stream comprising the organic substrate can be up or down flowed over a bed of catalyst at a liquid hourly space velocity (LHSV) of about 0.1 to about 20 hr$^{-1}$ preferably about 0.2 to about 10 hr$^{-1}$ and most preferably from about 0.5 to about 5 hr$^{-1}$. The imide can be part of the feedstream or be on the catalyst bed. The oxygen or oxygen containing compound can be introduced at one injection point or at multiple injection points. After the desired contact time, the reaction product can be separated from the rest of the reaction mixture and purified according to conventional techniques such as filtration, condensation, adsorption, distillation, extraction, crystallization, etc.

Usually the major or primary oxygenated product obtained from the instant process is either the corresponding ketone or aldehyde, although in some cases the corresponding alcohol or carboxylic acid can be the primary product. These oxygenated products, e.g. ketones, aldehydes can be used as is or can be converted to other products such as oximes, nitro-alkanes, amines, esters, alcohols, glycols, carboxylic acids and β-hydroxyesters. Preferably the oxygenated product is optionally reacted with a hydrogen containing gas in the presence of a hydrogenation catalyst to give the corresponding reduced oxygenated compound. A preferred reduced oxygenated compound is the corresponding alcohol. This can be carried out either before or after isolation of the reaction product. Again, the process can be carried out in a batch or continuous mode with continuous mode being preferred. Hydrogenation conditions include a temperature of about 20° C. to about 250° C., a pressure of about 340 kPa to about 28,000 kPa (50 to about 4,000 psig) and a liquid hourly space velocity of about 0.5 to about 10 hr$^{-1}$. In a batch mode the contact time varies from about 1 minute to about 5 hrs.

The hydrogenation catalyst comprises a hydrogenation component dispersed on a suitable support. Hydrogenation catalyst components include but are not limited to Group VIII metals of the Periodic Table, molybdenum, tungsten, nickel and mixtures thereof. Preferred hydrogenation components are the platinum group metals and nickel. The platinum group metals are platinum, palladium, rhodium, iridium, ruthenium and osmium. Preferred platinum group metals are platinum and palladium. The hydrogenation catalyst component is present in an amount from about 0.1 to about 10 wt. % as the metal. The support can be any support, which is inert to the reactants and products and has a sufficient surface area in order to disperse the hydrogenation component thereon. The surface area should be at least 5 m$^2$/g. Specific examples of supports include, but are not limited to, metal oxides, organic polymers, halogenated metal oxides, clays, carbon, and fluorinated carbon. These hydrogenation catalysts are prepared by conventional techniques in which one or more hydrogenation metal compounds are dissolved in a suitable solvent and then contacted with the support. Contacting can be done by impregnation, spray drying, etc. The final form of the hydrogenation component can be a metal, metal oxide or a metal compound.

The reduced oxygenated compound, e.g. alcohols, can be further dehydrated to give the corresponding olefin. Dehydration processes are well known in the art and involve contacting the reduced oxygenate with a dehydration catalyst at dehydration conditions. Dehydration catalysts include liquid and solid acid catalysts. Non-limiting examples include sulfuric acid, solid phosphoric acid, aluminas, amorphous silica-alumina, heteropolyacids, sulfated zirconia and zeolites. Dehydration conditions include a temperature of about 50° to about 400° C. and preferably from about 100° to about 250° C., a liquid hourly space velocity (LHSV) of about 0.1 to about 1000 hr$^{-1}$ and a pressure of about 10 to about 28,000 kPa. The weaker the acid strength, the higher the temperature required.

The following examples are presented in illustration of this invention and are not intended as undue limitations on the generally broad scope of the invention as set forth in the appended claims.

EXAMPLE 1

Preparation of N,N'-di-hydroxy-bicyclo[2.2.2]oct-7-ene-2,3,5,6 tetracarboxylic duimide.

To a round-bottomed flask equipped with a stirrer and a condenser, were added 0.21 g of anhydrous sodium carbonate and 12 g deionized water, followed by the addition of 0.29 g of hydroxylamine hydrochloride. After the exotherm had subsided 1 g of bicyclo[2.2.2]oct-7-ene-2,3,5,6-tetracarboxylic dianhydride was added. The resultant mixture was heated to 95° C. for 30 minutes and the duimide precipitated. The mixture was filtered warm, washed with deionized water and dried under nitrogen or vacuum. Note that the entire preparation was carried out under nitrogen. This material was identified as sample A.

EXAMPLE 2

Oxidation of dodecane was conducted as follows. Into a three-necked round-bottomed flask were added 0.138 g of sample A, 0.031 g cobalt acetyl-acetonate, 1.379 g of dodecane and 23.667 g of acetic acid. A thermometer, gas/vacuum inlet and a gas manometer were attached to the three necks. After the four components were added, the flask was sealed and the contents were frozen. The flask was next evacuated and then filled with oxygen. The evacuation/O$_2$ fill cycle was repeated for a total of 5 cycles. At the end of the fifth cycle the gas manometer was opened and the contents were heated to 100° C. with magnetic stirring. As the temperature increased, reaction began and the amount of oxygen consumed was recorded using the manometer. After about 4 hours, the reaction was stopped and the contents analyzed by gas chromatography (GC). The GC analysis showed that conversion of dodecane was 59% with 36% selectivity to ketones and 88% overall selectivity to oxygenates.

EXAMPLE 3

Oxidation of dodecane using N-hydroxy-phthalimide (NHPI) was conducted as follows. Into a three-necked round-bottomed flask were added 0.167 g of NHPI, 1.72 g of dodecane, 0.0292 g cobalt acetylacetonate and 21.5 g of acetic acid. A thermometer, gas/vacuum inlet and a gas manometer were attached to the three necks. After the four components were added, the flask was sealed and the contents were frozen. The flask was next evacuated and then filled with oxygen. The evacuation/O$_2$ fill cycle was repeated for a total of 5 cycles. At the end of the fifth cycle the gas manometer was opened and the contents were heated to 100° C. with magnetic stirring. As the temperature increased, reaction began and the amount of oxygen consumed was recorded using the manometer. After about 2 hours, oxygen uptake ceased at which point the reaction was stopped and the contents analyzed by gas chromatography (GC). The GC analysis showed that conversion of dodecane was 22% with 39% selectivity to ketones and 72% overall selectivity to oxygenates.

EXAMPLE 4

Into a four-neck round-bottomed flask equipped with a stirrer, dry airline and condenser were added 50 ml of sulfolane, 3.17 g of n-dodecane, 0.30 g of NHPI and 0.05 g of cobalt acetylacetonate. The solution was stirred to create a vortex and air was bubbled into the solution at a rate of about 80 ml/minute and the flask was heated to 100° C. Aliquots were periodically taken, via the fourth neck, and analyzed by gas chromatography.

The above experiment was repeated two more times except that glacial acetic acid and benzonitrile were used as the solvent.

The Figure presents curves of the total yield (based on area percent) of mono-ketones and mono-alcohols produced versus time. The plots show that using sulfolane increases the total yield of oxygenates versus acetic acid and benzonitrile.

We claim as our invention:

1. A process for converting an organic substrate to an oxygenated compound comprising reacting the organic substrate with an oxygen source in the presence of a catalyst comprising an imide promoter and a co-catalyst at oxidation conditions to provide an oxygenated compound, the imide promoter represented by at least one of structures (I), (II), (III) or (IV):

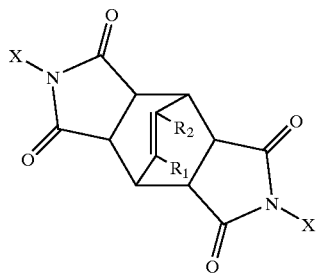
(I)

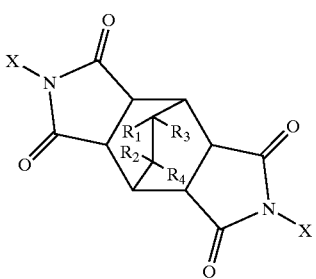
(II)

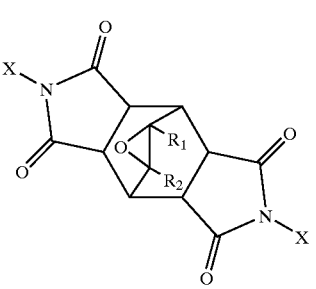
(III)

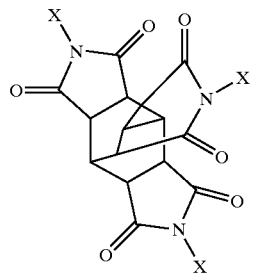
(IV)

where $R_1$, $R_2$, $R_3$ and $R_4$ are independently selected from the group consisting of hydrogen, halogens, alkyl groups, cycloalkyl groups, aryl groups, sulfonyl group, sulfonic acid, hydroxyl groups, alkoxy groups, carboxyl groups, ethers, amines, amides, alkoxy-carbonyl groups and acyl groups and X is selected from the group consisting of O, OH, acetyl, acetoxy, ether and halogen; and the co-catalyst comprising at least one metal selected from the group consisting of Groups IB, IVB, VB, VIB, VIIB and VIII, metals of the Periodic Table of the Elements.

2. The process of claim 1 where the imide promoter has structure (I).

3. The process of claim 2 where the imide promoter is N,N'-di-hydroxy-bicyclo[2.2.2]oct-7ene-2,3,5,6-tetracarboxylic diimide.

4. The process of claim 1 where the imide promoter has structure (II).

5. The process of claim 1 where the imide promoter has structure (III).

6. The process of claim 1 where the imide promoter has structure (IV).

7. The process of claim 1 where the oxidation conditions comprise a temperature of about 30° C. to about 300° C., a pressure of about 10 kPa to about 100 MPa and a contact time sufficient to convert the organic substrate to oxygenates.

8. The process of claim 7 where the process is carried out in a batch mode and the contact time varies from about 30 minutes to about 48 hours.

9. The process of claim 7 where the process is carried out in a continuous mode and at a liquid hourly space velocity of about 0.1 to about 20 $hr^{-1}$.

10. The process of claim 1 where the organic substrate is selected from the group consisting of aliphatic hydrocarbons, alicyclic hydrocarbons, heterocyclic compounds, alcohols, ethers, esters, ketones, aldehydes, amines and mixtures thereof.

11. The, process of claim 10 where the organic substrate is an aliphatic hydrocarbon having from 1 to 30 carbon atoms.

12. The process of claim 6 where the aliphatic hydrocarbon is a branched aliphatic hydrocarbon.

13. The process of claim 12 where the branch has one to 6 carbon atoms.

14. The process of claim 10 where the organic substrate is an alicyclic hydrocarbon having from 3 to 30 carbon atoms.

15. The process of claim 10 where the organic substrate is an aromatic hydrocarbon having at least one alkyl group attached thereto.

16. The process of claim 15 where the alkyl group has from 1 to 10 carbon atoms.

17. The process of claim 1 where the metal is present as a metal compound.

18. The process of claim 17 where the metal compound is a metal salt or a metal chelate.

19. The process of claim 18 where the salt is selected from the group consisting of acetate, nitrate, sulfate, carbonate and halide.

20. The process of claim 17 where the chelate is selected from the group consisting of acetylacetonate, porphyrins, phthalocyanines, crown ethers, ferrocene and mixtures thereof.

21. The process of claim 1 where the imide is present in an amount from about 0.05 to about 20 mole % with respect to the organic substrate.

22. The process of claim 1 where the metal is present in an amount from about 0.005 to about 0.015 mole % as the metal with respect to the organic substrate.

23. The process of claim 1 where the process is carried out in a solvent selected from the group consisting of carboxylic acids, hydroxycarboxylic acids, nitrites, sulfolane, substituted sulfolanes, amides, alkyl acetates and mixtures thereof.

24. The process of claim 23 where the solvent is sulfolane.

25. The process of claim 1 where the oxygen is present in an amount of oxygen: organic substrates of about 0.5:1 to 100:1.

26. The process of claim 1 further comprising reacting the oxygenated compound with hydrogen in the presence of a hydrogenation catalyst at hydrogenation conditions to provide an alcohol.

27. The process of claim 26 where the hydrogenation catalyst comprises a hydrogenation component selected from the group consisting of a Group VIII metal, molybdenum, tungsten, nickel and mixtures thereof.

28. The process of claim 26 where the hydrogenation conditions comprise a temperature of about 20° C. to about 250° C., a pressure of about 340 kPa to about 28,000 kPa and a liquid hourly space velocity of about 0.5 to about 10 $hr^{-1}$.

29. The process of claim 26 further comprising contacting the alcohol with a dehydration catalyst to provide an olefin.

30. The process of claim 29 where the dehydration catalyst comprises a liquid or solid acid.

31. The process of claim 30 where the dehydration catalyst is selected from the group consisting of sulfuric acid, solid phosphoric acid, aluminas, amorphous silica-alumina, heteropolyacids, sulfated zirconia and zeolites.

32. The process of claim 29 where the dehydration conditions comprise a temperature of about 50° C. to about 400° C., a LHSV of about 0.1 to about 1000 $hr^{-1}$ and a pressure of about 10 kPa to about 28,000 kPa.

* * * * *